(12) United States Patent
Leone et al.

(10) Patent No.: US 6,468,244 B1
(45) Date of Patent: Oct. 22, 2002

(54) CATHETER SYSTEM HAVING FULLERENES AND METHOD

(76) Inventors: James E. Leone, 5865 SW. 108th St., Miami, FL (US) 33156; Pallassana V. Narayanan, 911 Primrose CT., Belle Mead, NJ (US) 08502

( * ) Notice: Subject to any disclaimer, the term of this patent is extended or adjusted under 35 U.S.C. 154(b) by 0 days.

(21) Appl. No.: 09/555,793

(22) PCT Filed: Dec. 17, 1998

(86) PCT No.: PCT/US98/26814

§ 371 (c)(1),
(2), (4) Date: Jan. 5, 2000

(87) PCT Pub. No.: WO99/32184

PCT Pub. Date: Jul. 1, 1999

Related U.S. Application Data

(60) Provisional application No. 60/068,165, filed on Dec. 19, 1997.

(51) Int. Cl.[7] ............................................. A61M 29/00
(52) U.S. Cl. .................................. 604/103.02; 424/9.36
(58) Field of Search .............................. 600/116, 476, 600/478; 604/103.01, 103.02, 96.01, 65, 500, 508, 509, 103.05; 623/1.11, 1.12; 128/898; 424/9.3, 9.32

(56) References Cited

U.S. PATENT DOCUMENTS

| | | |
|---|---|---|
| 5,006,119 A | 4/1991 | Acker et al. |
| 5,090,959 A | 2/1992 | Samson et al. |
| 5,092,841 A | 3/1992 | Spears ................... 604/103.01 |
| 5,370,608 A | 12/1994 | Sahota et al. ................ 606/194 |
| 5,688,486 A | 11/1997 | Watson ...................... 424/9.36 |

FOREIGN PATENT DOCUMENTS

| | | |
|---|---|---|
| EP | 0 770 577 B1 | 5/1997 |
| WO | 95/21637 A1 | 8/1995 |

OTHER PUBLICATIONS

A.W. Jensen, et al., "Biological Applications Of Fullerenes"; Biorganic & Medical Chemistry, Elsevier Science Ltd, GB; vol. 4, No. 6, 1996, pp. 767–779; XP000964594; Department of Chemistry, New York University, 100 Washington Square East, New York, NY 10003.

Huei–Chen Huang, et al., "Antiproliferative Effect Of Polyhydroxylated C60 On Vascular Smooth Muscle Cells"; Electrochemical Society Proceedings, Electrochemical Society; vol. 3, 1996, pp. 403–410, XP000964676; Pennington, NJ.

*Primary Examiner*—Anhtuan T. Nguyen
(74) *Attorney, Agent, or Firm*—Michael W. Montgomery

(57) ABSTRACT

At least a portion of a catheter system (10) is provided with fullerene material (56) for performing or facilitating a medical procedure. In the case of a balloon catheter, the outer surface of the balloon may have a coating of fullerenes (64), which are preferably photosensitive or activated by light. A light source (60) can be used to illuminate or other wise activate the fullerene material. The light source (60) may be formed by one or more optical fibers extending through the shaft of the catheter, and into the balloon. Various arrangements of the catheter system are possible, whereby the light source may selectively emit light outward through the fullerene material, and associated portions of the catheter system, which may be translucent. When activated by light, the fullerene coating may preferably generate, and give off therapeutic oxygen radicals. These oxygen radicals may affect local cell function to prevent or reduce cell proliferation. This therapy may have many applications, including for example, limiting restenosis after angioplasty.

12 Claims, 3 Drawing Sheets

CATHETER SYSTEM HAVING FULLERENES AND METHOD

This application is a 371 PCT/US98/26814 filed Dec. 17, 1998 which claims benefit of provisional application Ser. No. 60/068,165 filed Dec. 19, 1997.

BACKGROUND AND DESCRIPTION OF THE INVENTION

1. Technical Background

The present invention relates generally to medical devices, and more particularly to a catheter having a portion coated with fullerenes, and therapeutic methods for making and using the same.

2. Discussion

Medical catheters are used in a variety of therapeutic applications, including esophageal catheters, urinary catheters, and intravascular catheters for procedures such as angioplasty. By way of example, the present invention will be described in relation to vascular catheters, and in particular intravascular balloon catheters. However, it should be understood that the present invention relates to any catheter or catheter system incorporating fullerenes, and is not limited to balloon catheters or any other type of catheter.

For example, most balloon catheters have a relatively long and flexible tubular shaft defining one or more passages, called lumens, an inflatable balloon at a forward or distal end connected to an inflation lumen extending through the shaft, leading to a proximal hub at the other end for connecting the shaft lumens to various equipment. Examples of this type of balloon catheter are shown in U.S. Pat. No. 5,304,197, entitled "Balloons For Medical Devices And Fabrication Thereof," issued to Pinchuk et al. on Apr. 19th, 1994, and U.S. Pat. No. 5,370,615, entitled "Balloons Catheter For Angioplasty," issued to Johnson on Dec. 6, 1994.

A common treatment method for using such a balloon catheter is to advance the catheter into the body of a patient, by directing the catheter distal end through an incision and along a body passage, until the balloon is located within the desired site. The term "desired site" refers to the location in the patient's body currently selected for treatment by a health care professional. After the balloon is disposed within the desired site, it can be selectively inflated for one of two basic purposes. First, the balloon may be used to temporarily block or occlude the body passage at a relatively low pressure, as in the case of a balloon made of elastic or compliant material. Second, the balloon can press outward on the wall of the body passage at relatively high pressure to a relatively constant diameter, as in the case of an inelastic or non-compliant balloon material.

This outward pressing of a constriction or narrowing at the desired site in a body passage is intended to partially or completely re-open or dilate that passageway or lumen, increasing its inner diameter or cross-sectional area. In the case of a blood vessel, this procedure is referred to as angioplasty, and it encourages greater blood flow through the newly expanded vessel. The narrowing of the lumen is called a lesion or stenosis, and may be formed of hard plaque or viscous thrombus.

Nearly one million angioplasties were performed worldwide in 1997 to treat vascular disease, including coronary, neurological and peripheral blood vessels partially or totally blocked or narrowed by a stenosis.

Unfortunately, within approximately six months after angioplasty, the lumen at the angioplasty site may re-close or narrow again. This phenomenon is called restenosis, and may occur in as many as 35% of percutaneous transluminal angioplasty patients. Restenosis may require an additional procedure, such as another angioplasty, drug therapy treatment, or surgery including bypass graft. It is of course desirable to prevent or limit the occurrence of restenosis, especially since some patients may not be preferred candidates for another interventional treatment.

One method of limiting restenosis is to permanently implant a cylindrical metal scaffold, referred to as a stent, into the vessel to hold the lumen open and improve blood flow. The presence of a stent tends to keep the blood vessel open longer, but their use can be limited by various factors, including size and location of the blood vessel, a complicated or tortuous vessel pathway, etc. Also, even a vessel with a stent may eventually develop restenosis.

A possible cause for restenosis is the proliferation of smooth muscle cells at the site of the lesion. In other words, a site where tissue has grown in the past, in the form of a collection of smooth muscle cells before angioplasty, may tend to accumulate cells at that location again. Accordingly, it is desirable to prevent or limit accumulation of these fast-replicating smooth muscle cells, in an effort to prevent restenosis.

It has been discovered that the local presence of oxygen radicals (or other reactive oxygen species) in the vicinity of a stenosis may kill smooth muscle cells, or inhibit their future accumulation. It is therefore desirable to provide a system or device and method for generating these oxygen radicals at the desired site within the patient's body.

It is possible that the presence of a newly discovered type of material may generate oxygen radicals or other reactive oxygen species when activated by exposure to light. This new class of materials is called "fullerenes," and they represent a previously unknown third form or allotrope of carbon. The other two carbon allotropes have been known for most of recorded history: graphite and diamond.

The family of fullerene materials includes a symmetrical hollow spherical molecule containing 60 carbon atoms ($C_{60}$), and also various asymmetrical forms, including carbon atoms in groups of 70, 76, 78, 82, 84, 90, and 96. The entire class of materials is named after the designer of the geodesic dome, R. Buckminster Fuller, because the spherical $C_{60}$ looks like a geodesic dome or soccer ball. Accordingly, $C_{60}$ is called Buckminsterfullerene or "bucky balls." The bucky ball is the only molecule of a single atom that forms a hollow spheroid shape, in geometric terms a "truncated icosahedon."

In 1985, Richard Smalley, Robert Curl, and Harold Kroto, won the Nobel Prize in chemistry for their work with fullerenes. This work led to various articles and patents, including U.S. Pat. No. 5,300,203, entitled "Process For Making Fullerenes By The Laser Evaporation Of Carbon," issued to Smalley on Apr. 5, 1994. A variety of compositions and different applications for fullerenes are described in many patents, including U.S. Pat. No. 5,172,278, entitled "Buckminsterfullerenes For Optical Limiters," issued to Tutt on Dec. 15, 1992, and U.S. Pat. No. 5,561,026, entitled "Photosensitive Materials Comprising Fullerenes," issued to Aoki on Oct. 1, 1996.

It is accordingly a general object of the present invention to provide a catheter system incorporating fullerenes for performing or facilitating a medical procedure.

These and various other objects, advantages and features of the invention will become apparent from the following description and claims, when considered in conjunction with the appended drawings.

DETAILED DESCRIPTION OF THE PREFERRED EMBODIMENTS

Figure 1:
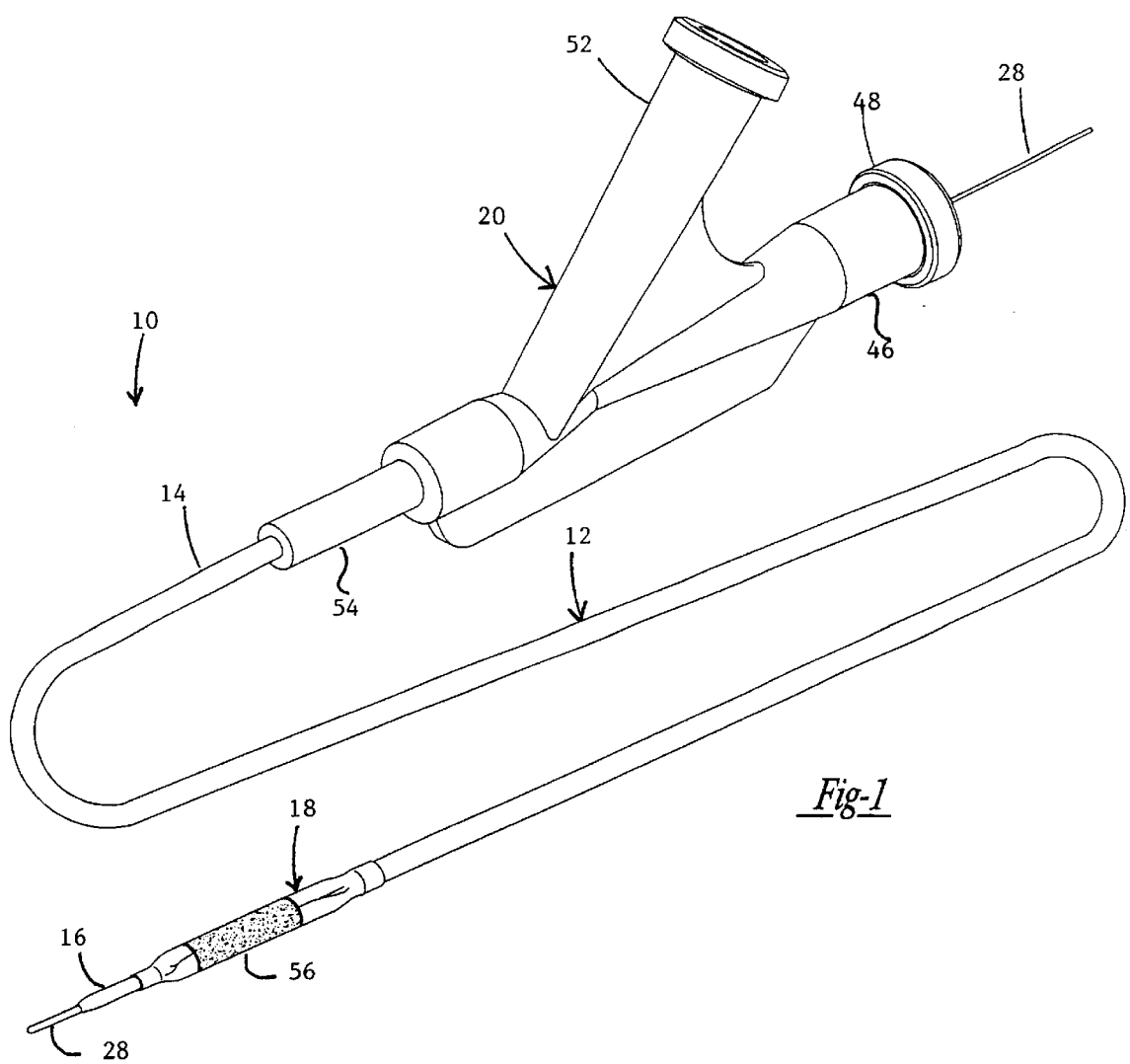
FIG. 1 is an external perspective view of a preferred catheter system including a balloon catheter having a fullerene coating around a portion of the balloon and a guidewire, arranged according to the principles of the present invention.

The following description of the preferred embodiments of the present invention is merely illustrative in nature, and as such it does not limit in any way the present invention, its application or uses. Numerous modifications may be made by those skilled in the art without departing from the true spirit and scope of the invention.

The present invention is a catheter system having fullerenes for performing or facilitating a medical procedure. Accordingly, the present invention may be used in conjunction with any suitable or desired set of catheter components and accessories, and it encompasses any of a multitude of catheter designs. These catheter designs may include for example a basic solid or tubular flexible catheter member, up to complex devices including multiple tubes or multiple extruded lumens, as well as various accessories such as guidewires, probes, ultrasound, optic fiber, electrophysiology, blood pressure or chemical sampling components. In other words, the present invention may be used in conjunction with any suitable catheter design, and is not limited to a particular type of catheter. With the understanding that the present invention relates to a catheter system for administering a medical therapy using fullerenes, the present invention will be described with reference to a particular preferred catheter design, in this case a balloon catheter.

With reference to the drawings, the balloon catheter is generally designated by reference numeral 10. Balloon catheter 10 has an elongated flexible catheter shaft 12 having a proximal end 14 as well as a distal end 16. Near the catheter distal end, an inflatable balloon 18 is affixed to the shaft, while a hub 20 is affixed to the opposing proximal end.

The shaft is preferably constructed of a pair of inner and outer coaxial tubes 22 and 24, such that the inner tube is received within and surrounded by the outer tube. The inner tube of course defines an inner lumen 26, which may be referred to as a "through" lumen or a "guidewire" lumen, and has an open distal port at the catheter distal end. A flexible guidewire 28 may be inserted and withdrawn through the guidewire lumen, to assist in steering and guiding the distal end of the catheter along a desired path. The outer and inner tubes cooperate to define an annular lumen 30, often called the "inflation" lumen, which opens at its distal end in communication with the interior 32 of the balloon.

The inflatable balloon preferably has a central cylindrical portion 34 flanked on both ends by proximal and distal transition zones 36 and 38, which connect the central portion to a pair of proximal and distal legs or collars 40 and 42. The proximal and distal legs are affixed to the outer and inner tubes of the catheter shaft in any suitable way, including by an adhesive or heat-seals.

One or more markers may be provided to indicate the location of portions of the catheter 10 under a viewing system, such as X-ray fluoroscopy. Such markers may take the form of metal marker bands 44 for marking the extent of the working portion of the balloon, or any other sort of marker for indication the position of a desired portion of the catheter 10 under whatever viewing system is likely to be used.

Figure 2:
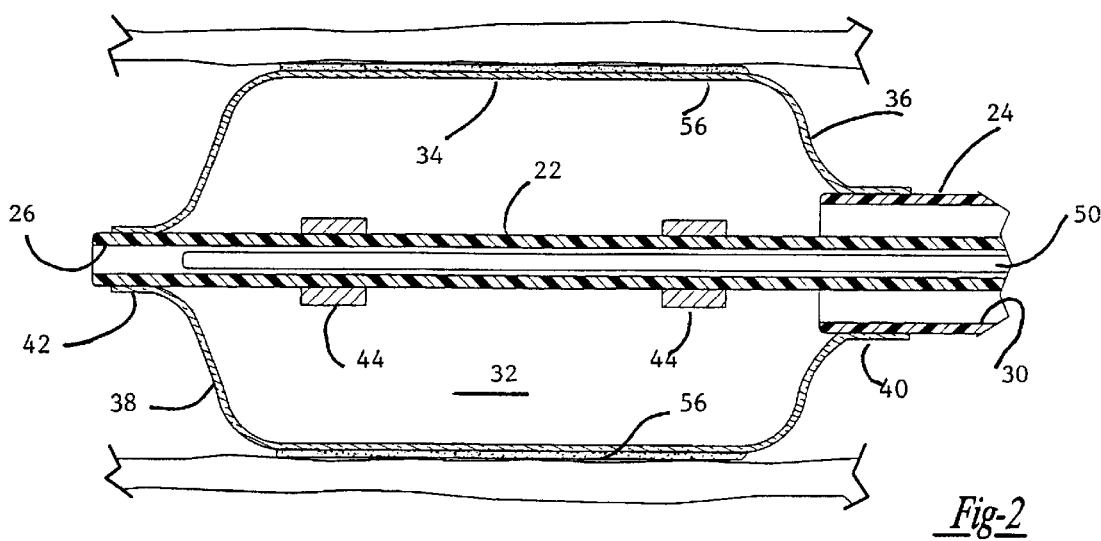
FIG. 2 is a partial longitudinal cross-section view of the catheter system of FIG. 1, depicting the balloon in an inflated condition within a body passageway.

The proximal hub provides couplers for connecting the lumens of the catheter shaft with other equipment. In the particular embodiment of the present invention, the hub connects the inner lumen to a proximal port 46 having a hemostatic valve 48, through which a guidewire 28, optical fiber or other device can be inserted. FIG. 1 depicts a guidewire 28, and FIG. 2 shows an optical fiber 50. The hemostatic valve 48 is of course designed to resist blood or other bodily fluids from escaping. The hub also connects the inflation lumen to an inflation port 52, for connection to a source of pressurized inflation fluid (not shown). A flexible strain relief 54 may be provided at the juncture between the hub and catheter shaft.

The shaft, balloon, hub, strain relief, and any other basic catheter components may be made of any suitable material by any desired method. For example, the balloon and shaft components may preferably be made of nylon or any other polymer having the desired properties, or some portion of the shaft may be made of a thin metal hypotube. Of course, the shaft may be made in various other ways, including a single tubular body extruded to define two parallel lumens. The shaft components may be coextruded of different materials, or the same material having different properties. The shaft may also include reinforcements or other structural components, including reinforcing coils or braiding.

The unique catheter system of the present invention is designed to deliver fullerene material to a particular site within the body of a patient. The fullerenes are adapted to have a therapeutic effect, or to otherwise perform or enhance a medical procedure. The therapeutic effect may include the generation of oxygen radicals or other reactive oxygen species, especially when the fullerenes are exposed to light or some other kind of activating energy.

In the specific embodiment depicted in FIGS. 1–2, the fullerene material has been supplied in the form of a fullerene coating 56 on the outer surface of a portion of the balloon 18. Fullerenes are available from Dynamic Enterprises, Ltd. in Berkshire, England: 44-118–9341500 (delEpncl.co.uk), and from Southern Chemical Group, LLC in Tucker, Ga.: (800) 958–2201 (scgchem@mindspring.com). Various techniques may be used to coat the fullerenes on a polymer substrate such as the balloon 18, including for example those described in U.S. Pat. No. 5,310,669 to Richmond et al., entitled "Fullerene Coated Surfaces And Uses Thereof" which issued on May 10, 1994.

The fullerene coating 56 is preferably applied to the central cylindrical segment of the balloon, so that when the balloon is inflated within the desired site for treatment, for example a blood vessel as in FIG. 2, the balloon wall expands and urges the fullerenes into contact with the desired site.

Figure 6:
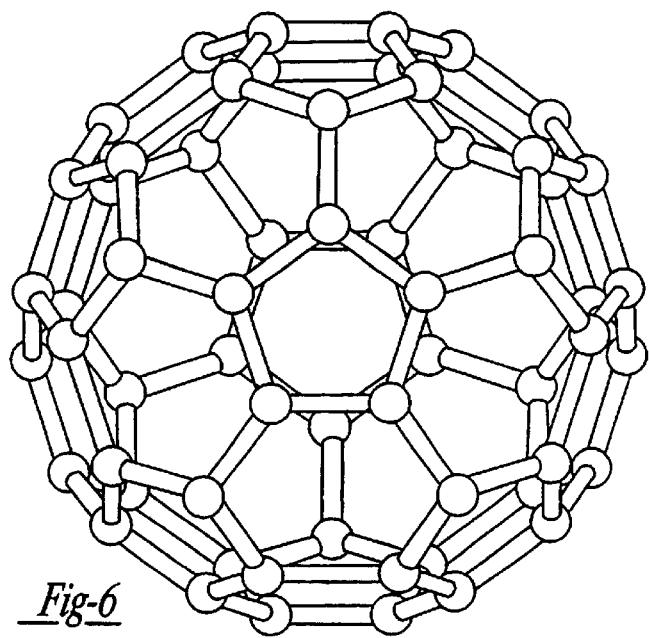
FIG. 6 is a diagrammatic view of a molecule of $C_{60}$ fullerene.

As described above, fullerene material may be provided in various molecular forms. FIG. 6 depicts a molecule of the perfectly spherical $C_{60}$, for example. It may be determined through further experimentation which of the fullerene molecules, or various combinations thereof, are preferable for specific therapeutic application. For example, an initial estimation of a composition which might be preferable includes 90% of the $C_{60}$ fullerene molecule combined with 10% of one or more of the other basic fullerene molecules, such as $C_{70}$, $C_{76}$, $C_{78}$, $C_{82}$, $C_{84}$, $C_{90}$, or $C_{96}$.

With the balloon inflated to an expanded shape and the fullerenes contacting the desired site as shown in FIG. 2, the fullerenes are preferably activated by exposing them to light or another form of activating energy. This energy may be visible light, or electromagnetic energy of any suitable type, including infrared or ultraviolet. Photosensitive fullerenes are described in U.S. Pat. No. 5,561,026 to Aoki, entitled "Photosensitive Materials Comprising Fullerene" which issued on Oct. 1, 1996.

The light or other form of activating energy may be provided from any suitable source, such as the optical fiber shown in FIGS. 1 and 2. The optical fiber can be inserted through the hemostatic valve and the inner lumen, until it is disposed within the balloon to better dissipate light in all radial directions, an illuminating portion of the fiber is preferably roughened as is known in the art.

When the fullerenes are thus activated, they may tend to generate oxygen radicals or other reactive oxygen species, or to otherwise have a therapeutic effect. This effect may include inhibiting the proliferation of cells, including smooth muscle cells, to resist restenosis.

Figure 3:
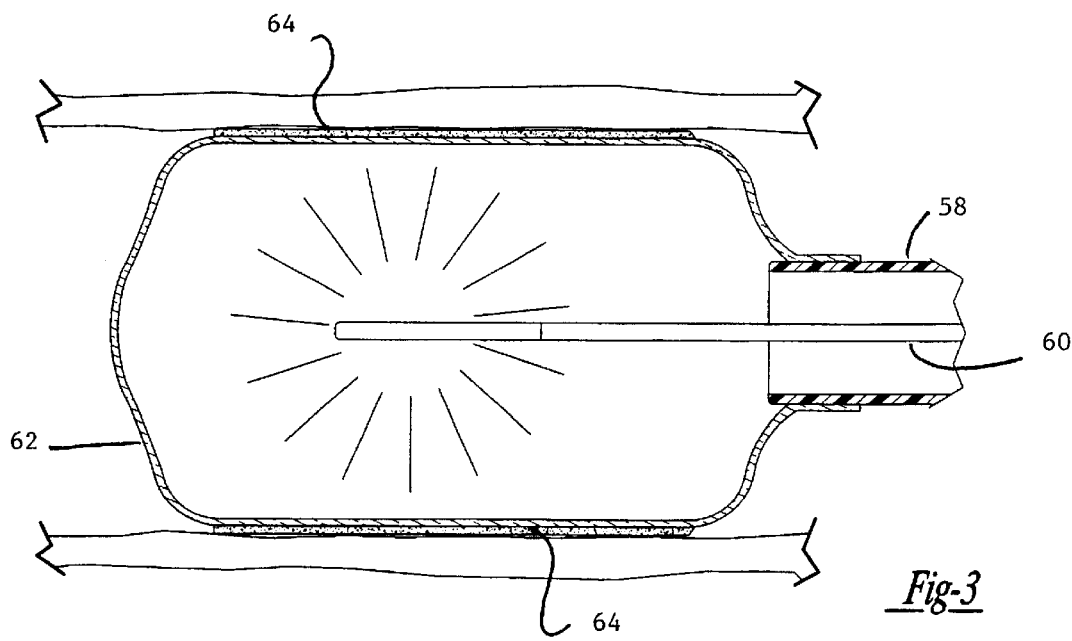
FIG. 3 is a partial longitudinal cross-section view of a balloon catheter system, according to another embodiment of the present invention.
Figure 4:
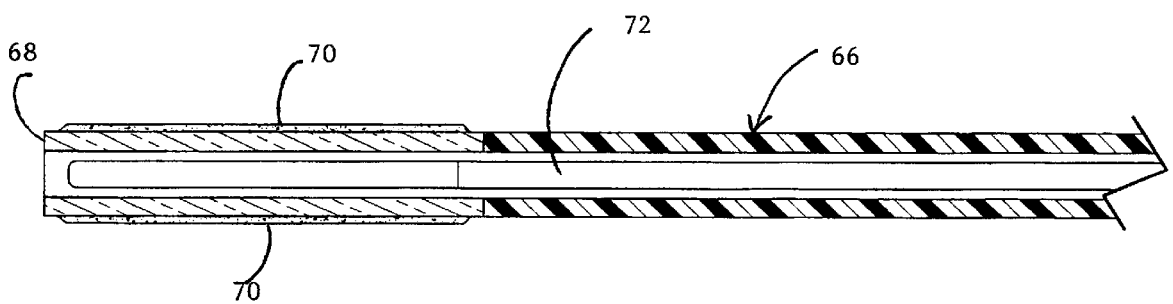
FIG. 4 is a partial longitudinal cross-section view of a catheter system according to yet another embodiment of the present invention.
Figure 5:
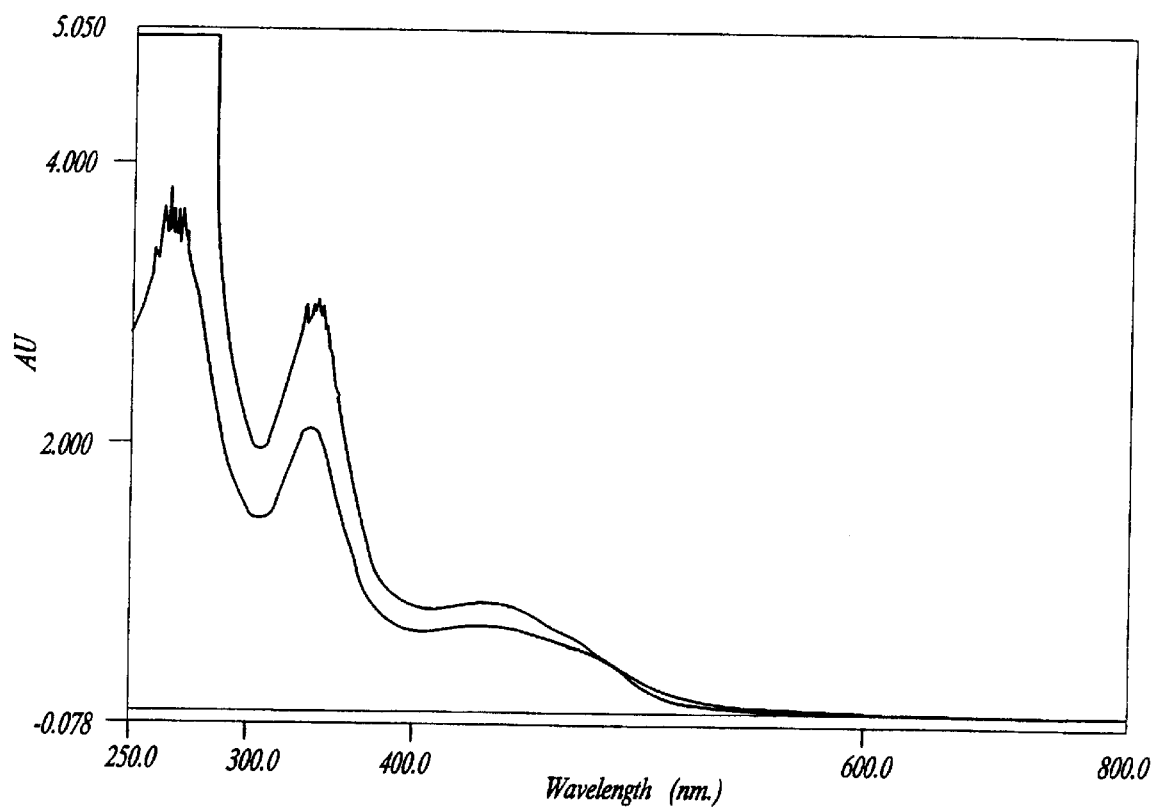
FIG. 5 is a diagrammatic view of absorption with respect to wavelength of a representative sample of fullerenes.

By way of example and to illustrate the wide range of possible catheter designs, a few alternative embodiments of the present invention are shown in FIGS. 3 and 4. The balloon catheter of FIG. 3 is a single-lumen design, having a simple and inexpensive tubular catheter shaft 58 defining a lumen, an optical fiber 60 extending therethrough which can be inserted or withdrawn, as well as a balloon 62 affixed to the distal end of the catheter shaft. The fullerene material 64 of the present invention may be coated or adhered to the outer surface of the balloon 62. This simpler embodiment might be used for treating areas of a patient's body that can be more easily accessed, without requiring use of a guidewire as shown in FIG. 1.

The embodiment of FIG. 4 is even more simple. This design may be preferred in a therapeutic application where a balloon as shown in FIGS. 1–3 is not necessary or desirable, or where the patient's anatomy is very narrow, or if it is discovered that placing the fullerenes in contact with the desired site unnecessary. This particular design includes a tubular shaft 66, of which a portion 68 is translucent or transparent. This translucent portion 68 of the tubular shaft 66 is coated with fullerene material 70, and a light source is provided within the translucent portion 68, in the form of an optical fiber 72 that may be slidably advanced within the tubular shaft.

Regardless of the design for the catheter system, any components located between the fullerene material and the light source should preferably be transparent or translucent to the activating energy. Accordingly, the catheter systems shown in FIGS. 1–4 incorporate transparent or translucent inner tube segments, balloons, or other tubes.

In addition, the fullerene material may of course be provided to the catheter system in any suitable manner, including mixing the fullerenes into a polymer and a perhaps a solvent, and then spraying, dipping, or otherwise applying the resulting material onto the appropriate catheter component.

It should be understood that an unlimited number of configurations for the present invention can be realized. The foregoing discussion describes merely exemplary embodiments of the principles of the present invention. Those skilled in the art will readily recognize from the description, claims, and drawings that numerous changes and modifications can be made without departing from the spirit and scope of the invention.

We claim:

1. A catheter system for providing medical treatment to a patient and reducing restenosis, comprising:
    a catheter having a therapy portion;
    an amount of fullerene material associated with the therapy portion;
    an amount of fullerene material associated with the therapy portion;
    a light source for illuminating the fullerene material;
    wherein the therapy portion and fullerene material in combination forms means for reducing a likelihood of restenosis from occurring at the local region of the therapy portion, the fullerene material being adapted to actively respond to such illumination to provide a medical therapy in the local region of the therapy portion.

2. The catheter system as set forth in claim 1, the catheter further comprising a catheter shaft defining an inflation lumen; wherein the therapy portion includes an inflatable balloon affixed to the distal end of the shaft and connected to the inflation lumen; and wherein the fullerene material is located on an outer surface of the balloon.

3. The catheter system as set forth in claim 1, wherein the catheter further comprises a catheter shaft defining a light lumen extending at least within the catheter therapy portion; and wherein the light source is adapted to extend within the light lumen.

4. The catheter system as set forth in claim 1, wherein at least the therapy portion of the catheter is translucent, and the fullerene material is located on an outer surface of the therapy portion, so that light from the light source can pass through the translucent therapy portion to activate the fullerene material.

5. The catheter system as set forth in claim 4, wherein the fullerene material actively responds to illumination of the light source by generating the formation of reactive oxygen species in the local region of the therapy portion.

6. The catheter system as set forth in claim 5, wherein the reactive oxygen species are specifically in the form of oxygen radicals.

7. An intravascular balloon catheter system for treating a patient's blood vessel comprising:
    a flexible catheter shaft having proximal and distal ends;
    a translucent balloon attached to the catheter shaft near its distal end;
    a light source within the balloon for selectively emitting light; and
    means for resisting restenosis, including a fullerene coating adhered to the outer surface of to balloon.

8. A medical therapy system for treating a site within the body of a
    patient by reducing restenosis, comprising:
    a catheter having a flexible catheter shaft with proximal and distal ends, a translucent balloon defining an interior volume attached to the catheter shaft near the distal end of the catheter shaft, and a restenosis-reducing fullerene coating on the outer surface of the balloon;

a first and second lumen defined by the catheter shaft, the first lumen opening into the interior of the balloon for allowing a pressurized fluid to selectively enter and exit the balloon to selectively inflate and deflate the balloon, the second lumen extending into the balloon interior volume, wherein a portion of said catheter shaft defines a portion of the second lumen that is translucent;

at least one light fiber having at least a portion extending through said second lumen into the balloon interior volume, said portion of said light fiber adapted to selectively emit light within the translucent portion of the second lumen, thereby illuminating at least a portion of balloon and fullerene coating; such that the coated balloon is adapted to inhibit restenosis.

9. The medical therapy system as set forth in claim 8, wherein the light emitted by the light fiber is in a non-visible portion of the spectrum.

10. An intravascular balloon catheter for treating a patient's blood vessel and reducing restenosis comprising:

a flexible catheter shaft with proximal and distal ends, a translucent balloon defining an interior volume attached to the catheter shaft near the distal end of the catheter shaft, and a fullerene coating on the outer surface of the balloon;

a first and second lumen defined by the catheter shaft, the first lumen into the interior of the balloon for allowing a pressurized fluid to selectively enter and exit the balloon to selectively inflate and deflate the balloon, the second lumen extending into the balloon interior volume, wherein a portion of said catheter shaft defines a portion of the second lumen that is translucent; and means for reducing restenosis.

11. A method of performing a medical treatment on a patient, comprising the steps of:

providing a catheter having a therapy portion with an amount of fullerene material;

illuminating the therapy portion and the fullerene material, to thereby activate the fullerene material and inhibit restenosis.

12. A method of medically treating a site within the vascular system of a patient, comprising the steps of:

a) introducing a predetermined amount of fullerenes into close proximity or direct contact with a site to be treated;

b) exposing said fullerenes to a selectively activated light source such that said fullerenes absorb light energy, whereby said fullerenes become active;

c) the active fullerenes then creating oxygen radicals in the local region near to the site; and d) the oxygen radicals acting to reduce a likelihood of restenosis from occurring at the site by inhibiting the proliferation of cells near the site.

* * * * *